United States Patent [19]

Baerns et al.

[11] Patent Number: 4,939,312

[45] Date of Patent: Jul. 3, 1990

[54] CONTINUOUS PROCESS FOR THE OXIDATIVE COUPLING OF METHANE TO $C_{2+}$ HYDROCARBONS IN THE PRESENCE OF CATALYSTS

[75] Inventors: Manfred Baerns, Äskulapweg 20, D-4630 Bochum 1; Joao A. da Silva Palla Carreiro, Dortmund; Wilfried Bytyn, Bochum, all of Fed. Rep. of Germany

[73] Assignee: Manfred Baerns, Bochum, Fed. Rep. of Germany

[21] Appl. No.: 910,872

[22] Filed: Sep. 23, 1986

[30] Foreign Application Priority Data

Sep. 27, 1985 [DE] Fed. Rep. of Germany ....... 3534530

[51] Int. Cl.$^5$ .............................................. C07C 2/00
[52] U.S. Cl. ................................................... 585/500
[58] Field of Search ............... 585/500, 943, 415, 417, 585/419, 700, 654, 656, 658

[56] References Cited

U.S. PATENT DOCUMENTS

| | | | |
|---|---|---|---|
| 4,495,374 | 1/1985 | Jones | 585/500 |
| 4,499,322 | 2/1985 | Jones | 585/500 |
| 4,523,049 | 6/1985 | Jones et al. | 585/943 |
| 4,523,050 | 6/1985 | Jones et al. | 585/943 |
| 4,547,608 | 10/1985 | Johnson | 585/500 |
| 4,547,611 | 10/1985 | Jones | 585/500 |
| 4,608,449 | 8/1986 | Baerns et al. | 585/500 |
| 4,620,057 | 10/1986 | Kimble | 585/500 |
| 4,654,459 | 3/1987 | Sofranko | 585/500 |
| 4,658,077 | 4/1987 | Kolts | 585/500 |

FOREIGN PATENT DOCUMENTS 0198251  3/1985  European Pat. Off. ............. 585/500
3237079  4/1984  Fed. Rep. of Germany .

OTHER PUBLICATIONS

Keller et al., "Synthesis of Ethylene via Oxidative Coupling of Methane", Journal of Catalysis, vol. 73, pp. 9–19 (1982).

Keller and Bhasin, "Synthesis of Ethylene via Oxidative Coupling of Methane", Journal of Catalysis, 73, 9–19 (1982).

Lunsford et al, Symposium on the New Surface Science in Catalysis Presented Before the Division of Colloid and Surface Chemistry, American Chemical Society, Philadelphia Meeting, Aug. 26–31, 1984, pp. 920–926.

Hinsen and Baerns, Oxidative Kopplung von Methan zu $C_2$-Kohlenwasserstoffen in Gegenwart unterschiedlicher Katalysatoren, Chemical Zeitung, 1983, pp. 223–226.

Primary Examiner—William R. Dixon, Jr.
Assistant Examiner—James M. Hunter, Jr.
Attorney, Agent, or Firm—Marshall, O'Toole, Gerstein, Murray & Bicknell

[57] ABSTRACT

A continuous process for the catalytic oxidative coupling in the presence of oxygen or an oxygen containing gas to $C_nH_m$ hydrocarbons ($n \geq 2$, $m = 2n$ or $2n+2$) at temperatures between 500° and 900° C., with partial pressures of methane above 0.5 bar and a ratio of the partial pressures of methane and oxygen between 1 and 20 is described. This process uses oxides, peroxides, hyperoxides, hydroxides, carbonates, sulfates, phosphates and silicates of the elements belonging to the 1., 2. and 4. main group of the periodic system as catalysts with and without a support material.

24 Claims, No Drawings

CONTINUOUS PROCESS FOR THE OXIDATIVE COUPLING OF METHANE TO $C_{2+}$ HYDROCARBONS IN THE PRESENCE OF CATALYSTS

The invention concerns the improvement of a process for the oxidative coupling of methane to $C_{2+}$ hydrocarbons ($C_{2+}$: $C_nH_m$ with $n \geq 2$ and $m=2n$ or $m=2n+2$) in the presence of oxygen or an oxygen containing gas at temperatures between 500° and 900° C., methane partial pressures above 0.5 bar and a ratio of methane to oxygen of at least 1, but preferably 2 to 20 by using new catalysts, which exhibit higher selectivities for the desired $C_{2+}$ hydrocarbons and also better stability of activity over long periods of time than those previously known.

BACKGROUND

In Offenlegungsschrift DE No. 32 37 079 A1 a process is described by which it is possible to convert methane in the presence of oxygen or an oxygen containing gas and in the presence of suitable catalysts at temperatures between 500° and 900° C. to ethane and ethylene according to the following chemical equation:

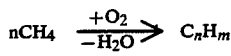

Besides the $C_{2+}$ hydrocarbons also undesired products i.e. CO and $CO_2$ can be formed.

By applying higher reaction temperatures the yield as well as the selectivity to $C_{2+}$ hydrocarbons, particularly to ethylene is increased. The catalysts used contain as catalytically active compounds the oxides of lead, antimonium, tin, bismut, cadmium, thallium, indium or their mixtures. The catalytically active compound may be used alone or together with one or several compounds being stable at higher temperatures and which are called support or support material. Such supports may be alumina, silica, titania, aluminum silicate or similar materials. Also some temperature resistant carbides like silicium carbide can be used. The use of a support is necessary to avoid sintering of the catalytically active compound when exposed to high temperatures in order to sustain a large surface area.

The oxides of several metals which can change their valency states under reaction conditions can directly be used as oxygen transferring materials for the oxidative coupling; they have, however, to be reoxidized. Such metals are antimonium (U.S. Pat. No. 4,443,644), germanium (U.S. Pat. No. 4,443,645), bismut (U.S. Pat. No. 4,443,646), lead (U.S. Pat. No. 4,443,647), indium (U.S. Pat. No. 4,443,648), manganese (U.S. Pat. No. 4,443,649) and tin (U.S. Pat. No. 4,444,984). The performance of such oxygen transferring agents which are no catalysts in the stricter sense of the words, can be improved by the addition of phosphates, alkali oxides (U.S. Pat. No. 4,499,322), alkaline earth oxides (U.S. Pat. No. 4,495,374), $CeO_2$ (U.S. Pat. No. 4,499,324), $RuO_2$ (U.S. Pat. No. 4,489,215) and $Pr_6O_{11}$ (U.S. Pat. No. 4,499,323).

Maximum selectivities for $C_{2+}$ hydrocarbons ($n \geq 2$) of approx. 50 to 70% were obtained in a continuous process for the oxidative coupling of methane when using catalysts containing PbO (comp. a) German patent application No. P 34 06 751.5 and (b) W. Hinsen, W. Bytyn, M. Baerns in Proceed. 8th Intern. Congr. Catal. 1984 Vol. III, p. 581, Verlag Chemie 1984).

There exists a certain disadvantage of such catalysts containing lead oxide or some of the other metal oxides mentioned above since their vapour pressures might not be negligible in some cases at the high reaction temperatures (>500° C.) required. High temperatures may result in a loss of catalytically active compound and leads eventually to deactivation. Furthermore, the deposition of lead or lead oxide or the other metals or metal oxides respectively in the cold parts of the production plant causes severe problems detrimental to smooth operation.

SUMMARY OF THE INVENTION

With the above background in mind, it is the purpose of the present invention to improve the process for the oxidative coupling of methane to higher hydrocarbons by the use of such catalysts which do not show any loss of catalytically active compounds and which furthermore result at the same time in better selectivities than had previously been attained with the above-mentioned catalysts.

DETAILED DESCRIPTION

The object of this invention is solved according to claim 1 of this invention. In a large number of experiments it was surprisingly observed, that on the one hand a group of completely new compounds or of such compounds, which have previously been mentioned only as promoters and which do not exhibit deactivation due to the disadvantageous volatility, result in better selectivities for the oxidative coupling than mentioned above and on the other hand, also lead can be used as a catalyst in the form of other compounds than in oxidic form which are not volatile. Furthermore, some of the new catalysts make it possible to use a lower ratio of methane to oxygen than previously applied when carrying out the oxidative coupling of methane; as a consequence the conversion of methane can be increased during passing through the reactor. This leads finally also to an improvement of the process economics.

Some of the catalytically active compounds mentioned in this invention have been already proposed as promoters, in particular the oxides of the alkali and alkaline earth metals; their inherent catalytic activity was, however, not recognized or was even excluded. Keller and Bhasin (J. Catal. 73, 9 (1982)) described the oxides of Li, Mg, Ca, Sr as substances which show only little or no activity and no selectivity for the oxidative coupling of methane; the present invention, however, leads to quite another result. Ito and Lunsford (Nature 314, 721 (1985)) mentioned, that MgO and $Li_2O$ and $Li_2CO_3$ respectively can be used only as a mixture for the oxidative coupling; again, the present invention shows, that lithium compounds as such can be used as catalysts. Contradictory to the opinion of Ito and Lunsford lithium compounds result in good selectivities, even when used with a support material like $\alpha\text{-}Al_2O_3$. Even better selectivities are achieved when using LiOH and $Li_2SO_4$ instead of lithium oxide. Finally, Ito and Lunsford (J. Am. Chem. Soc. 107, 58 (1985)) assume, similar to Keller and Bhasin, that sodium compounds do not provide good selectivity. Again, this is a contradiction to the results of the present invention.

The oxidative coupling of methane is performed under the conditions already mentioned above. That is at 500° to 900° C., with total pressures from 1 to 5 bar— whereby there is in principle no upper limit for the total pressure—and with ratios of the partial pressures of methane and oxygen larger than 1, preferentially above 2 to 10. The conversion is carried out in catalytic fixed bed reactors with or without partial recycle of the reaction mixture, in catalytic fluidized bed reactors or in cross-flow reactors (DE No. 32 32 079 A1 and German pat. appl. No. P 34 06 751.5).

According to the invention the catalytically active compounds are the oxides, peroxides, hyperoxides, hydroxides, carbonates, sulfates, phosphates and/or silicates of elements of the 1., 2. and 4. main group of the periodic system. These compounds can be used individually or as mixtures. Particularly good catalytic properties for the oxidative methane coupling exhibit the following substances $Li_2O$, $LiOH$, $Li_2SO_4$, $Na_2O$, $Na_2O_2$, $NaO_2$, $NaOH$, $Na_2SO_4$, $Nap_2CO_3$, $K_2O$, $K_2O_2$, $KOH$, $K_2SO_4$, $K_2CO_3$, $MgSO_4$, $Mg_3(PO_4)_2$ magnesium silicate, $CaSO_4$, $Ca_3(PO_4)_2$, calcium silicate, $SrO$, $SrO_2$, $SrCO_3$, $SrSO_4$, $Sr_3(PO_4)_2$, $BaO$, $BaO_2$, $BaCO_3$, $Ba_3(PO_4)_2$, $PbSO_4$, $Pb_3(PO_4)_2$, lead silicate.

Some of the individual substances mentioned above are thermally and/or mechanically not stable; catalyst particles disintegrate or sinter. Therefore, these catalytically active compounds are used together with support materials and/or structural promoters. Those compounds that have a stability satisfactory for the use as a catalyst, can be applied with or without support material. A support should fulfil certain criteria: (a) it should have a large internal surface area to ascertain a satisfactory activity, (b) selectively active surface sites of the catalytic compounds must not be disadvantageously modified by the support, (c) it should exhibit thermal and-mechanic stability, (d) it should have mainly macropores and no micropores.

Suitable as a support material are those compounds which have already been described previously i.e. alpha, eta and gamma alumina, silica, silicium carbide or titania. Of particular interest as support materials or structural promoters are such substances which exhibit an inherent catalytic activity and selectivity for methane coupling. Such compounds are $MgO$, $CaO$, $CaSO_4$, $Ca_3(PO_4)_2$ as well as calcium and magnesium silicates. Not suited as support materials are, however, such compounds, which exhibit strong surface acidity like aluminum silicate since their acidic sites which favour the non-selective oxidation can be hardly neutralized by additional compounds. Therefore support materials on the basis of magnesium and calcium compounds are preferred which exhibit a certain surface basicity and which have an inherent catalytic activity.

Activity and selectivity of a supported catalyst can depend on the percentage of the catalytic compound on the support; there exists an optimum composition for each catalyst.

The experimental results on which the present invention is based can be explained and summarized as follows:

(a) Oxygen containing solids which can give off their lattice oxygen easily, exhibit poorer selectivities than those which have a stronger affinity to their lattice oxygen. This is exemplified for lead compounds; their selectivity obeys the following order:

$PbSO_4 > PbO > PbMoO_4$ (b) Catalytically active compounds exhibiting a high surface acidity which can be attributed to acidic Broensted sites like aluminum silicate yield almost exclusively CO and $CO_2$ when converting methane with oxygen. The selectivity towards $C_{2+}$ hydrocarbons is below 10%.

(c) Catalytically active compounds which exhibit a high surface concentration of acidic or basic Lewis sites like precalcined gamma-$Al_2O_3$ and also $CaO$, result in $C_{2+}$ selectivities up to approximately 60%.

(d) Catalytically active compounds which exhibit a high surface concentration of basic Broensted sites lead to $C_{2+}$ selectivities of nearly 100%. Such catalytically active solids are those compounds which exist under reaction conditions partly or as a whole in the form of hydroxides like alkali hydroxides, alkali oxides as well as $SrO$ and $BaO$.

From the above statements it may be concluded, that the catalytic performance of the various solids for the oxidative coupling of methane depends significantly on the type and strength of surface acidity and basicity which in turn can be affected by the preparation method.

PREPARATION OF CATALYSTS

When using acidic support materials (like gamma-$Al_2O_3$) extended periods of drying (at ca 110° to 140° C.) of the impregnated support and simultaneously extended times of calcination (temperature 10° to 60° C. above reaction temperature) are required. Those times are in the order of 30 to 48 hrs.

In contrast, when using basic, catalytically active compounds and/or supports (e.g. $CaO$) such treatment conditions have to be chosen which ascertain a high Broensted basicity of the catalysts. The periods of drying (at 110°-130° C.) should be short (2-24 hrs.) or can be even omitted when no disadvantages with respect to mechanical stability of the catalyst are caused. The thermal treatment (calcination) occurs also under mild conditions, i.e. the calcination temperature corresponds to reaction temperature and the duration 2-24 hrs. Preferentially, these catalysts are used immediately for the oxidative coupling of methane after drying.

A. Single Components

The single components are either commercially available preparations or are compounds produced by the usual processes.

B. Mixed and Supported Catalysts

The following methods were used in the production of the mixed and supported catalysts forming the basis of this invention:

(b 1) Dry impregnation: a solution of the component or components to be applied is added to a carrier material or to one of the catalytically active components until the solid does not absorb any more liquid.

(2) Wet impregnation: the carrier substance is suspended in a solution of the compound to be applied and the liquid evaporated to dryness with stirring.

(3) Mechanical mixing of the compounds to be used wherein in some cases the mixture thus obtained is subsequently impregnated with bidistilled water.

A catalyst can be produced in multi-stage processes wherein different methods can be used in each step. The methods (1) to (3) are simply serve as practical examples and are thus not exclusive or binding.

The catalysts used have the composition shown in Table 1. The preparation of a larger number of catalysts is described in the following.

Catalyst K-1

BeO was a commercial sample (Merck, 99% purity). This catalyst was used without pretreatment.

Catalyst K-2

$BeSO_4$ was obtained by dehydration of $BeSO_4.4H_2O$ (Merck, 99% purity) under reaction conditions.

Catalyst K-3

MgO was produced by decomposition of magnesium hydroxycarbonate (Merck, p.a., 24% Mg content) under reaction conditions.

Catalyst K-4

MgO was produced by decomposition of $Mg(OH)_2$ (Merck, purest) under reaction conditions.

Catalyst K-5

$MgSO_4$ was produced by dehydration of $MgSO_4.7H_2O$ (Baker Chemicals, 100% purity) under reaction conditions.

Catalyst K-6

CaO was obtained by decomposition of $CaCO_3$ (Riedel de Haen, p.a.) under reaction conditions.

Catalyst K-7

CaO was obtained by decomposition of $Ca(OH)_2$ (Riedel de Haen, 96% purity) under reaction conditions.

Catalyst K-8

$CaSO_4$ was produced by thermal decomposition of $CaSO_4.0.5\ H_2O$ (technical) under reaction conditions.

Catalyst K-9

$SrCO_3$ was a commercial preparation (Riedel de Haen, 99% purity). This catalyst was used without pretreatment.

Catalyst K-10

SrO was obtained by decomposition of $Sr(OH)_2.8H_2O$ (Merck, 97% purity) under reaction conditions.

Catalyst K-11

SrO was produced by thermal decomposition of $Sr(OH)_2.8H_2O$ in a weak air stream at 700° C. (4 hrs.), and subsequently at 800° C. (4 hrs.) and finally at 950° C. (19 hrs.).

Catalyst K-12

$SrSO_4$ was a commercial preparation (Fluka AG, pract.). This catalyst was used untreated.

Catalyst K-13

$BaSO_4$ was a commercial preparation (Riedel de Haen, chem. pure). It was used untreated.

Catalyst K-14

BaO was produced by decomposition of $Ba(NO_3)_2$ (Riedel de Haen, 99% purity) in an air stream at 800° C. (4 hrs.).

Catalyst K-15

$K_2CO_3$ was a commercial preparation. (Riedel de Haen, 99% pure). It was measured without pretreatment.

Catalyst K-16

$Na_2CO_3$ was a commercial preparation (Merck, 100% purity). It was used untreated.

Catalyst K-17

This catalyst was produced by thorough grinding of 1.02 g $K_2CO_3$ (K-16) with 4.1 g SrO (K-11). This corresponds to a composition of 19.9 wt-% $K_2CO_3$/SrO.

Catalyst K-18

1 g lead (IV) acetate (Janssen) was dissolved in 50 ml benzene (J. T. Baker, 99% purity to be used) and added to 9.7 g $K_2CO_3$. The suspension was concentrated and the residue dried at 120° C. for 16 hrs. at 750 Torr and 7 hrs. at ca. 15 Torr and finally calcined for 24 hrs. at 500° C. This catalyst then contained 4.9 wt-% PbO/$K_2CO_3$.

Catalyst K-19

2.6 g $(NH_4)_2SO_4$ (technical product) were dissolved in 50 ml bidistilled water. 1.85 g magnesium hydroxycarbonate were dry impregnated with this solution. Use amounted to 4.46 ml. The catalyst was dried at 130° C. (14 hrs.) and calcined at 500° C. (16 hrs.). The composition corresponds to 22.4 wt-% $MgSO_4$/MgO.

Catalyst K-20

5.16 g $MgSO_4.7H_2O$ were dissolved in 50 ml bidistill water. 1.4 g magnesium hydroxycarbonate were dry impregnated with this solution. Use amounted to 3.79 ml. The catalyst was dried for 14 hrs. at 130° C. and subsequently calcined for 16 hrs. at 500° C. in a weak air stream. The composition corresponds to 26.8 wt-% $MgSO_4$/MgO.

Catalyst K-21

1.44 g $Na_2SO_4$ (Roth, 99.5% purity) were dissolved in 50 ml bidistilled water. 5.0 g $MgSO_4.7H_2O$ were dry impregnated. Use amounted to 0.47 ml. The catalyst was dried for 18 hrs. at 130° C. and calcined for 21 hrs. at 500° C. The composition corresponds to 0.5 wt-% $Na_2SO_4$/$MgSO_4$.

Catalyst K-22

2.63 g NaOH (Riedel de Haen, 98.5% purity) were dissolved in 50 ml bidistilled water. 3.84 g $Ca(OH)_2$ were dry impregnated with this alkali. Use amounted to 2.33 ml. The catalyst was dried at 130° C. (24 hrs.) and calcined at 800° C. (12 hrs.) in a weak air stream. The composition corresponds to 4.0 wt-% NaOH/CaO.

Catalyst K-23

2.76 g NaOH were dissolved in 50 ml bidistilled water. 10.72 g $Ca(OH)_2$ were dry impregnated with this alkali. Use amounted to 6.40 ml. The catalyst was dried for 4 hrs. at 130° C. and subsequently used without further pretreatment. The composition corresponded to 4.2 wt-% NaOH/CaO.

Catalyst K-24

This catalyst was produced by intimate grinding of 1.6012 g SrO (K-11), 0.803 g $K_2CO_3$ and 1.602 g of catalyst K-22. The composition was then as follows: 1.6 wt-% NaOH - 20.0 wt-% $K_2CO_3$ - 38.4 wt-% CaO - 40.0 wt-% SrO.

Catalyst K-25

5.99 g Si(OC$_2$H$_5$)$_4$ (Merck, 97% purity) and 30 ml ethanol (absolute, J. T. Baker, 99.5% purity to be used) were added to 4.26 g Ca(OH)$_2$ and the thus obtained suspension evaporated three times using 50 ml bidistilled water each time. The catalyst was dried for 50 hrs. at 130° C. and calcined for 23 hrs. at 800° C. in a weak air stream.

Catalyst K-26

This catalyst was produced by intimately grinding 4.81 g PbO (Riedel de Haen, 99% purity) with 2.42 g CaO (Riedel de Haen).

Catalyst K-27

7.7 g lead nitrate (Riedel de Haen, 100% purity; were dissolved in 50 ml bidistilled water. 2.1 g Ca$_2$SiO$_4$ (K-25) were dry impregnated with this solution. Use amounted to 3.46 ml. The catalyst was subsequently dried at 130° C. (69 hrs.) and calcined at 800° C. in a weak air stream (25 hrs.). The composition corresponds to 14.8 wt-% PbO/Ca$_2$SiO$_4$.

Catalyst K-28

4.8 g lead nitrate were dissolved in 50 ml bidistilled water. 10.0 g CaSO$_4$.0.5H$_2$O were dry impregnated with this solution. Use amounted to 8.27 ml. The catalyst was dried for 42 hrs. at 130° C. and subsequently calcined for 26 hrs. at 800° C. in a weak air stream. The composition corresponds to 5.1 wt-% PbO/CaSO$_4$.

Catalyst K-29

31 g lead nitrate were dissolved in 200 ml bidistilled water. 50 ml portions of this solution were mixed with 150 ml 1% sulfuric acid. The suspensions thus arising were each warmed for 5 min. with stirring and the precipitate subsequently filtered-off and dried for 17 hrs. at 130° C. The dry powder was finally mixed with 9.1% of its weight polyethylene, and processed to pellets which were calcined for 21.5 hrs. at 800° C.

Catalyst K-30

23.93 g PbO were ground with 5.72 g P$_2$O$_5$ and subsequently calcined for 68 hrs. at 800° C. in a weak air stream.

Catalyst K-31

0.43 g of dried PbSO$_4$ (K-29) were mixed with 1.0 g Ca$_3$(PO$_4$)$_2$ (J. T. Baker) and ground. This corresponds to 30.1 wt-% PbSO$_4$/Ca$_3$(PO$_4$)$_2$.

Catalyst K-32

0.703 g of dried PbSO$_4$ (K-29) were ground with 2.319 g CaSO$_4$.0.5 H$_2$O and then dry impregnated with bidistilled water (1.83 ml). The catalyst was dried for 14 hrs. at 130° C. and calcined for 23 hrs. at 800° C. in a weak air stream. This corresponds to 22.1 wt-% PbSO$_4$/CaSO$_4$.

Catalyst K-33

This catalyst was prepared exactly as K-32 but with 0.219 g PbSO$_4$ and 9.881 g CaSO$_4$.0.5H$_2$O. Water use amounted to 4.14 ml. This corresponds to 2.0 wt-% PbSO$_4$/CaSO$_4$.

Catalyst K-34

0.708 g Sr (OH)$_2$.8 H$_2$O were mixed with 3.964 g Ca(OH)$_2$. Ca. 20 ml H$_2$O were added. The suspension was evaporated, dried at 130° C. (20 hrs.) and calcined at 800° C. (16 hrs.). This corresponds to a composition of 8.4 wt-% SrO/CaO.

Catalyst K-35

0.0769 g LiOH were mixed with 4.015 g Ca(OH)$_2$ and subsequently dry impregnated with bidistilled water (2.45 ml). The catalyst was dried at 130° C. (21.5 hrs.) and calcined at 800° C. in a weak air stream (20.5 hrs.). This corresponds to a composition of 2.5 wt-% LiOH/CaO.

Catalyst K-36

4.02 g Ca(OH)$_2$ were dry impregnated with a solution of 6.63 g potassium nitrate (Riedel de Haen, 99% purity) in 50 ml bidistilled water. Use amounted to 2.56 ml. The catalyst was subsequently dried at 130° C. (22.5 hrs.) and calcined in a weak air stream at 800° C. (20.5 hrs.).

Catalyst K-37

A mixture of 4.0 g Ca(OH)$_2$ and 0.279 g Na$_2$SO$_4$ were dry impregnated with 2.81 ml bidistilled water. The catalyst was dried for 2 hrs. at 130° C. This corresponds to a composition of 8.4 wt-% Na$_2$SO$_4$/CaO.

Catalyst K-38

4.57 g lithium nitrate (J. T. Baker, 97% purity) were dissolved in 50 ml bidistilled water. 6.03 g Ca(OH)$_2$ were dry impregnated with this solution. Use amounted to 3.82 ml. The catalyst was dried for 2 hrs. at 130° C. This corresponds to 1.6 wt-% Li$_2$O/CaO.

Catalyst K-39

3.47 g Na$_2$CO$_3$ were dissolved in 50 ml bidistilled water. 4.49 g Ca(OH)2 were dry impregnated with this solution. Use amounted to 3.28 ml. The catalyst was dried for 21.5 hrs. at 130° C. and subsequently calcined for 17.5 hrs. at 800° C. in a weak air stream. The composition corresponds to 6.3 wt-% Na$_2$CO$_3$/CaO.

Catalyst K-40

A mixture of 4.01 g Ca(OH)$_2$ and 0.328 g K$_2$SO$_4$ was dry impregnated with 2.53 ml bidistilled H$_2$O. The catalyst was dried for 22.2 hrs. at 130° C. and calcined for 21.5 hrs. at 800° C. in a weak air stream. The composition corresponds to 9.8 wt-% K$_2$SO$_4$/CaO.

Catalyst K-41

3.705 g KOH were dissolved in 50 ml bidistilled water. 4.617 g Ca(OH)$_2$ were dry impregnated with this alkali. Use amounted to 2.88 ml. The catalyst was dried for 21.5 hrs. at 130° C. and subsequently calcined for 17.5 hrs. at 800° C. in a weak air stream. The composition corresponds to 5.8 wt-% KOH/CaO.

Catalyst K-42

5.56 g NaNO$_3$ (technical preparation were dissolved in 50 ml bidistilled water. 4.455 g Ca(OH)$_2$ were dry impregnated with this solution. Use amounted to 2.81 ml. The catalyst was dried for 22.2 hrs. at 130° C. and calcined for 21.5 hrs. at 800° C. in a weak air stream. The composition corresponds to 3.3 wt-% Na$_2$O/CaO.

Catalyst K-43

4.64 g $K_2CO_3$ were dissolved in 50 ml bidistilled $H_2O$. 4.09 g $Ca(OH)_2$ were dry impregnated with this solution. Use amounted to 2.98 ml. The catalyst was dried for 21.5 hrs. at 130° C. and subsequently calcined for 17.5 hrs. at 800° C. in a weak air stream. This corresponds to a composition of 8.2 wt-% $K_2CO_3/CaO$.

Catalyst K-44

A mixture of 4 g $Ca(OH)_2$ and 0.101 g $Li_2SO_4.H_2O$ (Merck, 99% purity) was dry impregnated with 2.86 ml bidistilled distilled $H_2O$. The catalyst was dried for 2 hrs. at 130° C. The composition corresponds to 2.8 wt-% $Li_2SO_4/CaO$.

Catalyst K-45 gamma-$Al_2O_3$ (Merck, water free) was calcined for 45 hrs. at 1150° C. in a weak air stream.

Catalyst K-46

A mixture comprising 4.04 g alpha-$Al_2O_3$ (K-45) and 1.08 g $Na_2SO_4$ was dry impregnated with 2.42 ml bidistilled $H_2O$. The catalyst was dried for 24 hrs. at 130° C. and calcined for 17.5 hrs. at 800° C. in a weak air stream. The composition corresponds to 21.1 wt-% $Na_2SO_4/Al_2O_3$.

Catalyst K-47

A mixture of 0.42 g LiOH and 5.35 g alpha-$Al_2O_3$ (K-45) was dry impregnated with 3.40 ml bidistilled water. The catalyst was dried for 54 hrs. at 130° C. at water jet pump pressure and calcined for 21 hrs. at 950° C. in a weak air stream. The composition corresponds to 7.3 wt-% $LiOH/Al_2O_3$.

EXAMPLES

For the oxidative coupling with the described catalysts a tubular reactor is used in which the catalyst existed either in fines or pellets. The reaction mixture consisting of methane and air as the oxidizing agent was passed through the reactor which contained the catalyst. The gas leaving the reactor was analyzed by gas-chromatography for $H_2$, $O_2$, $N_2$, CO, $CO_2$ as well as $C_2$ to $C_6$ hydrocarbons. The water which was formed by the reaction was condensed and tested for formaldehyde. $CH_2O$ as well as $C_5$ and $C_6$ hydrocarbons were not present at al or only in negligible traces.

The experimental conditions of the various experiments are listed together with the results in Table 2. The degree of oxygen conversion and of methane conversion and the selectivity for the various products are defined as follows:

$$X_{O2} = \frac{\Sigma s_i n_i}{n^o_{O2}} \times 100$$

$$X_{CH4} = \frac{\Sigma j_i n_i}{n^o_{CH4}} \times 100$$

$$S_i = \frac{j_i n_i}{\Sigma j_i n_i} \times 100$$

$n_i$ are the moles of formed products with $j_i$ carbon atoms; $s_i$ is the number of water molecules formed for the hydrocarbon product i. $S_{HC}$ is the total selectivity for the formation of hydrocarbons.

TABLE 1

Experimental conditions and results on oxidative methane coupling in obtained a plug flow reactor

| Catalyst Designat. | $P^o_{CH4}$ <bar> | $P^o_{O2}$ <bar> | $T_{max}$ <°C.> | W/F <g.s/ml> | $X_{O2}$ <%> | $X_{CH4}$ <%> | $S_{HC}$ <%> | $S_{CO}$ <%> | $S_{CO2}$ <%> | $S_{C2H4}$ <%> | $S_{C2H6}$ <%> | $S_{(C3+C3=)}$ <%> | $S_{(C4+C4=)}$ <%> |
|---|---|---|---|---|---|---|---|---|---|---|---|---|---|
| K-1 | 0,65 | 0,078 | 744 | 3,44 | 99 | 9 | 24 | 29 | 47 | 9 | 15 | 0,2 | — |
| K-2 | 0,68 | 0,068 | 745 | 20,51 | 87 | 15 | 6 | 62 | 33 | 1 | 5 | — | — |
| K-3 | 0,64 | 0,080 | 607 | 1,27 | 93 | 8 | 2 | 8 | 90 | 0,2 | 1,7 | — | — |
| K-3 | 0,64 | 0,078 | 650 | 0,46 | 97 | 9 | 18 | 19 | 63 | 4 | 13 | 0,4 | — |
| K-3 | 0,67 | 0,073 | 700 | 0,21 | 91 | 9 | 40 | 15 | 45 | 12 | 26 | 1,4 | — |
| K-3 | 0,65 | 0,077 | 740 | 0,22 | 94 | 11 | 53 | 10 | 37 | 20 | 32 | 1,5 | — |
| K-4 | 0,64 | 0,078 | 753 | 0,62 | 95 | 10 | 22 | 27 | 51 | 8 | 14 | 0,1 | — |
| K-4 | 0,47 | 0,116 | 760 | 0,64 | 96 | 19 | 21 | 23 | 56 | 10 | 11 | 0,2 | — |
| K-5 | 0,65 | 0,077 | 745 | 9,64 | 38 | 3 | 60 | 6 | 34 | 20 | 39 | 1,3 | — |
| K-6 | 0,64 | 0,079 | 786 | 0,19 | 96 | 12 | 51 | 7 | 42 | 15 | 34 | 1,4 | — |
| K-7 | 0,65 | 0,080 | 771 | 0,15 | 94 | 14 | 54 | 14 | 32 | 18 | 34 | 2,1 | — |
| K-8 | 0,63 | 0,080 | 744 | 10,61 | 53 | 7 | 53 | 3 | 44 | 22 | 28 | 2,6 | — |
| K-9 | 0,63 | 0,080 | 741 | 3,62 | 64 | 7 | 40 | 9 | 51 | 12 | 28 | 1,3 | — |
| K-10 | 0,65 | 0,076 | 746 | 7,15 | 99 | 13 | 55 | 3 | 42 | 29 | 21 | 3,2 | 1,6 |
| K-11 | 0,77 | 0,055 | 850 | 3,86 | 100 | 8 | 97 | 1 | 2 | 53 | 37 | 6,1 | 0,8 |
| K-12 | 0,63 | 0,078 | 742 | 25,98 | 100 | 13 | 8 | 1 | 91 | 3 | 5 | — | — |
| K-13 | 0,63 | 0,082 | 740 | 18,18 | 21 | 2 | 34 | 35 | 31 | 10 | 24 | — | — |
| K-14 | 0,65 | 0,079 | 740 | 17,75 | 93 | 10 | 99 | — | 1 | 43 | 46 | 6,5 | 3,1 |
| K-15 | 0,60 | 0,086 | 743 | 4,40 | 97 | 12 | 38 | 1 | 61 | 13 | 25 | 0,8 | — |
| K-16 | 0,64 | 0,078 | 747 | 56,04 | 71 | 10 | 51 | 6 | 43 | 28 | 19 | 4,2 | 0,3 |
| K-17 | 0,65 | 0,077 | 740 | 42,10 | 96 | 7 | 98 | — | 2 | 52 | 36 | 5,9 | 5,0 |
| K-18 | 0,67 | 0,066 | 742 | 8,40 | 99 | 13 | 67 | — | 33 | 26 | 35 | 4,0 | 1,1 |
| K-19 | 0,67 | 0,073 | 746 | 3,54 | 39 | 4 | 66 | 22 | 12 | 23 | 41 | 2,2 | — |
| K-20 | 0,65 | 0,077 | 744 | 8,52 | 65 | 10 | 65 | 28 | 17 | 27 | 20 | 3,8 | 2,8 |
| K-21 | 0,66 | 0,076 | 744 | 25,64 | 39 | 3 | 46 | 37 | 17 | 23 | 19 | 3,4 | — |
| K-22 | 0,64 | 0,079 | 748 | 0,79 | 98 | 16 | 69 | 1 | 30 | 24 | 39 | 5,0 | 1,3 |
| K-22 | 0,47 | 0,118 | 750 | 1,44 | 88 | 22 | 57 | 1 | 42 | 22 | 29 | 4,4 | 1,0 |
| K-22 | 0,31 | 0,153 | 744 | 2,95 | 100 | 39 | 44 | 1 | 54 | 23 | 18 | 3,0 | 0,9 |
| K-23 | 0,66 | 0,074 | 771 | 0,19 | 97 | 15 | 77 | 1 | 22 | 25 | 44 | 4,4 | 3,2 |
| K-23 | 0,68 | 0,071 | 840 | 0,16 | 100 | 15 | 78 | — | 22 | 28 | 41 | 2,7 | 5,8 |
| K-24 | 0,62 | 0,081 | 740 | 38,39 | 94 | 6 | 99 | 0,2 | 0,2 | 50 | 39 | 6,2 | 4,9 |
| K-25 | 0,63 | 0,079 | 777 | 0,20 | 100 | 11 | 43 | 3 | 54 | 12 | 30 | 1,2 | — |
| K-26 | 0,64 | 0,081 | 754 | 1,34 | 100 | 13 | 48 | — | 48 | 13 | 36 | 2,8 | — |

TABLE 1-continued

Experimental conditions and results on oxidative methane coupling in obtained a plug flow reactor

| Catalyst Designat. | $P^0_{CH4}$ <bar> | $P^0_{O2}$ <bar> | $T_{max}$ <°C.> | W/F <g.s/ml> | $X_{O2}$ <%> | $X_{CH4}$ <%> | $S_{HC}$ <%> | $S_{CO}$ <%> | $S_{CO2}$ <%> | $S_{C2H4}$ <%> | $S_{C2H6}$ <%> | $S_{(C3+C3=)}$ <%> | $S_{(C4+C4=)}$ <%> |
|---|---|---|---|---|---|---|---|---|---|---|---|---|---|
| K-27 | 0,65 | 0,079 | 781 | 0,20 | 94 | 9 | 46 | 1 | 53 | 9 | 36 | 1,4 | — |
| K-28 | 0,67 | 0,074 | 747 | 9,92 | 99 | 12 | 60 | 1 | 39 | 26 | 29 | 3,8 | 1,0 |
| K-29 | 0,66 | 0,074 | 741 | 30,67 | 63 | 8 | 63 | 6 | 31 | 32 | 23 | 5,0 | 3,2 |
| K-30 | 0,66 | 0,072 | 746 | 49,48 | 40 | 5 | 42 | 4 | 54 | 12 | 29 | 0,5 | — |
| K-30 | 0,64 | 0,084 | 847 | 19,94 | 79 | 12 | 63 | 7 | 30 | 32 | 23 | 6,7 | — |
| K-31 | 0,64 | 0,079 | 744 | 2,44 | 89 | 12 | 60 | 1 | 39 | 25 | 32 | 2,0 | 1,2 |
| K-32 | 0,65 | 0,074 | 743 | 11,59 | 33 | 4 | 62 | 11 | 27 | 23 | 37 | 2,4 | — |
| K-33 | 0,86 | 0,033 | 745 | 14,26 | 100 | 6 | 75 | 1 | 24 | 23 | 48 | 3,3 | 0,6 |
| K-34 | 0,64 | 0,078 | 754 | 0,84 | 100 | 13 | 57 | 1 | 42 | 16 | 37 | 2,8 | 0,6 |
| K-35 | 0,64 | 0,079 | 743 | 1,05 | 99 | 13 | 70 | 1 | 29 | 24 | 38 | 3,9 | 2,9 |
| K-36 | 0,65 | 0,077 | 758 | 0,38 | 86 | 10 | 56 | 3 | 41 | 14 | 40 | 2,0 | — |
| K-37 | 0,66 | 0,075 | 783 | 0,25 | 92 | 16 | 78 | 4 | 18 | 26 | 45 | 4,8 | 2,2 |
| K-38 | 0,66 | 0,077 | 753 | 0,50 | 97 | 14 | 72 | 1 | 28 | 24 | 40 | 4,0 | 3,4 |
| K-39 | 0,66 | 0,077 | 749 | 0,49 | 98 | 13 | 67 | 1 | 32 | 20 | 41 | 3,2 | 2,5 |
| K-40 | 0,66 | 0,077 | 757 | 0,42 | 93 | 14 | 74 | 2 | 24 | 24 | 42 | 4,2 | 3,2 |
| K-41 | 0,66 | 0,077 | 752 | 0,47 | 93 | 11 | 59 | 2 | 39 | 18 | 37 | 2,4 | 1,6 |
| K-42 | 0,65 | 0,077 | 745 | 0,47 | 95 | 10 | 54 | 1 | 45 | 16 | 36 | 2,3 | — |
| K-43 | 0,65 | 0,077 | 751 | 0,48 | 94 | 10 | 59 | 1 | 40 | 13 | 33 | 1,2 | — |
| K-44 | 0,65 | 0,080 | 745 | 0,91 | 98 | 14 | 74 | 3 | 23 | 32 | 34 | 4,6 | 3,8 |
| K-45 | 0,63 | 0,078 | 746 | 1,10 | 99 | 11 | 42 | 11 | 42 | 14 | 31 | 1,3 | — |
| K-46 | 0,65 | 0,078 | 743 | 1,92 | 93 | 11 | 59 | 3 | 38 | 19 | 36 | 1,6 | 1,4 |
| K-47 | 0,63 | 0,078 | 745 | 6,88 | 100 | 11 | 54 | 6 | 40 | 24 | 26 | 1,9 | 2,3 |

What we claim is:

1. A continuous process for the heterogeneously catalyzed oxidative coupling of methane in the presence of oxygen or an oxygen-containing gas to $C_n H_m$ hydrocarbons ($n \geq 2$, $m = 2n$ or $2n+2$) the steps of which comprise, introducing methane and oxygen or an oxygen-containing gas into a reactor, maintaining reaction zone conditions of temperatures between 500° and 900° C., methane partial pressures larger than 0.5 bar and a ratio of partial pressures of methane and oxygen or an oxygen-containing gas with supported or unsupported catalysts, comprising oxides, peroxides, hyperoxides, hydroxides, carbonates, sulfates, phosphates and silicates of elements selected from the group consisting of Li, Na, K, Rb, Cs and Be, peroxides, hyperoxides, hydroxides, carbonates, sulfates, phosphates and silicates of elements selected from the group consisting of Sr and Ba and the carbonates, sulfates, phosphates and silicates of elements selected from the group consisting of Pb, Sn, Ge, Mg and Ca.

2. A process according to claim 1 wherein the catalysts are supported by a carrier selected from the group consisting of $Al_2O_3$, $SiO_2$, SIC and $TiO_2$.

3. A continuous process for the heterogeneously catalyzed oxidative coupling of methane in the presence of oxygen or an oxygen-containing gas to $C_nH_M$ hydrocarbons (($n \geq 2$, $m=2n$ or $2n+2$) the steps of which comprise, introducing methane and oxygen or an oxygen-containing gas into a reactor, maintaining reaction zone conditions of temperatures between 500° C. and 900° C., methane partial pressures larger than 0.5 bar and a ratio of partial pressures of methane and oxygen between 1 and 20, and contacting methane and oxygen or an oxygen-containing gas with supported or unsupported catalysts, comprising oxides, peroxides, hyperoxides, hydroxides, carbonates, sulfates, phosphates and silicates of elements selected from the group consisting of Li, Na, K, Rb, Cs and Be, peroxides, hyperoxides, hydroxides, carbonates, sulfates, phosphates and silicates of elements selected from the group consisting of Sr and Ba and the carbonates, sulfates, phosphates and silicates of elements selected from the group consisting of Pb, Sn, Ge, Mg and Ca.

4. A process according to claim 3 wherein the oxides, peroxides, hyperoxides, hydroxides, carbonates, sulfates, phosphates and silicates of elements selected from the group consisting of Li, Na, K, Rb, and Cs and the peroxides, hyperoxides, hydroxides, carbonates, sulfates, phosphates and silicates of the elements selected from the group consisting of Sr and Ba and the carbonates, sulfates, phosphates and silicates of elements selected from the group consisting of Mg, Ca and Pb or their mixtures are used as catalysts.

5. A process according to claim 3 wherein compounds selected from the group consisting of $Li_2O$, LiOH, $Li_2SO_4$, $Na_2O$, $Na_2O_2$, $NaO_2$, NaOH, $Na_2SO_4$, $Na_2CO_3$, $K_2O$, $K_2O_2$, KOH, $KSO_4$, $K_2CO_3$ and their mixtures are used as catalysts.

6. A process according to claim 3 wherein compounds selected from the group consisting of $MgSO_4$, $Mg_3(PO_4)_2$, magnesia silicate, $CaSO_4$, $Ca_3(PO_4)_2$, calcium silicate, $SiO_2$, $SrCO_3$, $SrSO_4$, $Sr_3(PO_4)_2$, $BaO_2$, $DaCO_3$, $BaSO_4$, $Ba_3(PO_4)_2$ and their mixtures are use as catalysts.

7. A process according to claim 3 wherein compounds selected from the group consisting of $PbSO_4$, $Pb_3(PO_4)_2$, lead silicate and their mixtures are used as catalysts.

8. A process according to claim 3 using as catalysts mixtures of catalytically active compounds selected from the group consisting of $Li_2O$, LiOH, $Li_2SO_4$, $Na_2O$, $Na_2O_2$, $NaO_2$, NaOH, $Na_2SO_4$, $Na_2CO_3$, $K_2O$, $K_2O_2$, KOH, $K_2SO_4$, $K_2CO_3$ and mixtures thereof; and catalytically active compounds selected from the group consisting of $MgSO_4$, $Mg_3(PO_4)_2$, magnesia silicate, $CaSO_4$, $Ca_3(PO_4)_2$, calcium silicate, $SrO_2$, $SrCO_3$, $SrSO_4$, $Sr_3(PO_4)_2$, $BaO_2$, $BaCO_3$, $BaSO_4$, $Ba_3(PO_4)_2$ and mixtures thereof.

9. A process according to claim 3 using as catalysts mixtures of catalytically active compounds selected from the group consisting of $Li_2O$, LiOH, $Li_2SO_4$, $Na_2O$, $Na_2O_2$, $NaO_2$, NaOH, $Na_2SO_4$, $Na_2CO_3$, $K_2O$, $K_2O_2$, KOH, $K_2SO_4$, $K_2CO_3$ and mixtures thereof; and catalytically active compounds selected from the group consisting of the compounds $PbSO_4$, $Pb_3(PO_4)_2$, lead silicate and mixtures thereof.

10. A process according to claim 3 using as catalysts mixtures of catalytically active compounds selected from the group consisting of $MgSO_4$, $Mg_3(PO_4)_2$, magnesia silicate, $CaSO_4$, $Ca_3(PO_4)_2$, calcium silicate, $SrO_2$, $SrCO_3$, $SrSO_4$, $Sr_3(PO_4)_2$, $BaO_2$, $BaCO_3$, $DaSO_4$, $Ba(PO_4)_2$ and mixtures thereof; and catalytically active compounds selected from the group consisting of $PbSO_4$, $Pb_3(PO_4)_2$, lead silicate and mixtures thereof.

11. A process according to claim 3 using as catalysts mixtures of catalytically active compounds selected from the group consisting of $Li_2O$, $LiOH$, $Li_2SO_4$, $Na_2O_2$, $NaO_2$, $NaOH$, $Na_2SO_4$, $Na_2CO_3$, $K_2O$, $K_2O_2$, $KOH$, $K_2SO_4$, $K_2CO_3$ and mixtures thereof; catalytically active compounds selected from the group consisting of $MgSO_4$, $Mg_3(PO_4)_2$, magnesia silicate, $CaSO_4$, $Ca_3(PO_4)_2$, calcium silicate, $SrO_2$, $SrCO_3$, $SrSO_4$, $Sr(PO_4)_2$, $BaO_2$, $BaCO_3$, $BaSO_4$, $Ba_3(PO_4)_2$ and mixtures thereof; and catalytically active compounds selected from the group consisting of $PbSO_4$, $Pb_3(PO_4)_2$, lead silicate and mixtures thereof.

12. A process according to claim 10 wherein $PbSO_4$ mixed with a compound selected from the group consisting of $CaSO_4$ and $Ca_3(PO_4)_2$ is used as a catalyst.

13. A process according to claim 3 wherein the catalysts are supported by a carrier selected from the group consisting of $Al_2O_3$, $SiO_2$, $SiC$ and $TiO_2$.

14. A continuous process for the heterogeneously catalyzed oxidative coupling of methane in the presence of oxygen or an oxygen-containing gas to $C_n H_m$ hydrocarbons ($n \geq 2$, $m = 2n$ or $2n+2$) the steps of which comprise, introducing methane and oxygen or an oxygen-containing gas into a reactor, maintaining reaction zone conditions of temperatures between 500° and 900° C., methane partial pressures larger than 0.5 bar and a ratio of partial pressures of methane and oxygen between 1 and 20, and containing methane and oxygen or an oxygen-containing gas with supported or unsupported catalysts, comprising oxides, peroxides, hyperoxide, hydroxides, carbonates, sulfates, phosphates and silicates of elements selected from the group consisting of Li, Na, K, Rb, Cs and Be, and the carbonates, sulfates, phosphates and silicates of elements selected from the group consisting of PB, Sn, Ge, Mg, Ca, Ba and Sr.

15. A process according to claim 14 where in the oxides, peroxides, hyperoxides, hydroxides, carbonates, sulfates, phosphates and silicates of elements selected from the group consisting of Li, Na, K, Rb, and Cs and the carbonates, sulfates, phosphates and silicates of elements selected from the group consisting of Mg, Ca, Sr, Ba and Pb or their mixtures are used as catalysts.

16. A process according to claim 14 wherein compounds selected from the group consisting of $Li_2O$, $LiOH$, $Li_2SO_4$, $Na_2O$, $Na_2O_2$, $NaO_2$, $NaO_2$, $NaOH$, $NaSO_4$, $Na_2CO_3$, $K_2O$, $K_2O_2$, $KOH$, $K_2SO_4$, $K_2CO_3$ and their mixtures are used as catalysts.

17. A process according to claim 14 wherein compounds selected from the group consisting of $MgSO_4$, $Mg_3(PO_4)_2$, magnesia silicate, $CaSO_4$, $Ca(PO_4)_2$, calcium silicate, $SrCO_3$, $SrSO_4$, $Sr_3(PO_4)_2$, $BaCO_3$, $BaSO_4$, $Ba(PO_4)_2$ and their mixtures are used as catalysts.

18. A process according to claim 14 wherein compounds selected from the group consisting of $PbSO_4$, $Pb_3(PO_4)_2$, lead silicates and their mixtures are used as catalysts.

19. A process according to claim 14 using as catalysts mixtures of catalytically active compounds selected from the group consisting of $Li_2O$, $LiOH$, $Li_2SO_4$, $Na_2O$, $Na_2O_2$, $NaO_2$, $NaOH$, $Na_2SO_4$, $NaCO_3$, $K_2O$, $K_2O_2$, $KOH$, $K_2SO_4$, $K_2CO_3$ and mixtures thereof; and catalytically active compounds selected from the group consisting of $MgSO_4$, $Mg_3(PO_4)_2$, magnesia silicate, $CaSO_4$, $Ca_3(PO_4)_2$, calcium silicate, $SrCO_3$, $SrSO_4$, $Sr_3(PO_4)_2$, $BaCO_3$, $BaSO_4$, $Da_3(PO_4)_2$ and mixtures thereof.

20. A process according to claim 14 using as catalysts mixtures of catalytically active compounds selected from the group consisting of $Li_2O$, $LiOH$, $LiSO_4$, $Na_2O$, $Na_2O_2$, $NaO_2$, $NaOH$, $Na_2SO_4$, $Na_2CO_3$, $K_2O$, $K_2O_2$, $KOH$, $K_2SO_4$, $K_2CO_3$ and mixtures thereof; and catalytically active compounds selected from the group consisting of the compounds $PbSO_4$, $Pb_3(PO_4)_2$, lead silicate and mixtures thereof.

21. A process according to claim 14 using as catalysts mixtures of catalytically active compounds selected from the group consisting of $MgSO_4$, $Mg_3(PO_4)_2$, magnesia silicate, $CaSO_4$, $Ca_3(PO_4)_2$, calcium silicate, $SrCO_3$, $SrSO_4$, $Sr_3(PO_4)_2$, $BaCO_3$, $BaSO_4$, $Ba_3(PO_4)_2$ and mixtures thereof; and catalytically active compounds selected from the group consisting of $PbSO_4$, $Pb_3(PO_4)_2$, lead silicate and mixtures thereof.

22. A process according to claim 14 using as catalysts mixtures of catalytically active compounds selected from the group consisting of $Li_2O$, $LiOH$, $Li_2SO_4$, $Na_2O$, $Na_2O_2$, $NaO_2$, $NaOH$, $Na_2SO_4$, $Na_2CO_3$, $K_2O$, $K_2O_2$, $KOH$, $K_2SO_4$, $K_2CO_3$ and mixtures thereof; catalytically active compounds selected from the group consisting of $MgSO_4$, $Mg_3(PO_4)_2$, magnesia silicate, $CaSO_4$, $Ca_3(PO_4)_2$, calcium silicate, $SrCO_3$, $SrSO_4$, $Sr_3(PO_4)_2$ $BaCO_3$, $BaSO_4$,$Ba_3(PO_4)_2$ and mixtures thereof; and catalytically active compounds selected from the group consisting of $PBSO_4$, $Pb_3(PO_4)_2$, lead silicate and mixtures thereof.

23. A process according to claim 21 wherein $PbSO_4$ mixed with a compound selected from the group consisting of $CaSO_4$ and $Ca(PO_4)_2$ is used as a catalyst.

24. A process according to claim 14 wherein the catalysts are supported by a carrier selected from the group consisting of $Al_2O_3$, $SiO_2$, $SiC$ and $TiO_2$.

* * * * *

UNITED STATES PATENT AND TRADEMARK OFFICE
CERTIFICATE OF CORRECTION

PATENT NO. : 4,939,312

DATED : July 3, 1990

INVENTOR(S) : Baerns, et al.

It is certified that error appears in the above-identified patent and that said Letters Patent is hereby corrected as shown below:

Column 3, line 17, "$Nap_2CO_3$" should be --$Na_2CO_3$--.

Column 3, line 34, "and-mechanic" should be --and mechanic--.

Column 4, line 51, "(b1)" should be --(1)--.

Column 4, line 55, between "impregnation" and "the", insert --:-- (a colon).

Column 5, line 5, "Catalyst K-2" should be centered.

Column 6, line 30, "bidistill" should be --bidistilled--.

Column 6, line 41, "$MgSO_4.7H_2$ O" should be --$MgSO_4.7H_2O$--.

Column 8, line 40, "Ca(OH)2" should be --$Ca(OH)_2$--.

Column 8, line 63, after "preparation", insert --)--.

Column 9, line 4, "Ca(OH)2" should be --$Ca(OH)_2$--.

Column 9, line 13, delete "distilled".

Column 10, line 15, "al" should be --all--.

Column 10, line 27 (equation), "CH4" should be --$CH_4$--.

Column 11, line 31, "Cn Hm" should be --$C_nH_m$--.

Column 11, line 33, delete the comma between "comprise" and "introducing".

UNITED STATES PATENT AND TRADEMARK OFFICE
CERTIFICATE OF CORRECTION

PATENT NO. : 4,939,312

DATED : July 3, 1990

INVENTOR(S) : Baerns, et al.

It is certified that error appears in the above-identified patent and that said Letters Patent is hereby corrected as shown below:

Column 11, line 37, after "oxygen" insert --between 1 and 20, and contacting methane and oxygen--.

Column 11, lines 42-45, after "Cs", delete "Be, Sr and Ba, and carbonates, sulfates, phosphates and silicates, phosphates and silicates of elements selected from the group consisting of Pb, Sn, Ge, Mg and Ca.".

Column 11, line 50, "SIC" should be --SiC--.

Column 11, line 53, "$C_nH_M$" should be --$C_nH_m$--.

Column 11, line 54, "((" should be --(--.

Column 12, line 42, "$KSO_4$" should be --$K_2SO_4$--.

Column 12, line 47, "$SiO_2$" should be --$SrO_2$--.

Column 12, line 48, "$DaCO_3$" should be --$BaCO_3$--.

Column 12, line 48, "use" should be --used--.

Column 13, line 8, "$DaSO_4$" should be --$BaSO_4$--.

Column 13, lines 8-9, "$Ba(PO_4)_2$" should be --$Ba_3(PO_4)_2$--.

Column 13, lines 14-15, between "$Li_2SO_4$" and "$Na_2O_2$", insert --$Na_2O$--.

Column 13, line 20, "$Sr(PO_4)_2$" should be --$Sr_3(PO_4)_2$--.

Column 13, line 39, "containing" should be --contacting--.

Column 13, line 46, "PB" should be --Pb--.

UNITED STATES PATENT AND TRADEMARK OFFICE
CERTIFICATE OF CORRECTION

PATENT NO. : 4,939,312

DATED : July 3, 1990

INVENTOR(S) : Baerns, et al.

It is certified that error appears in the above-identified patent and that said Letters Patent is hereby corrected as shown below:

Column 13, line 47, "where in" should be --wherein--.

Column 13, line 56, "$NaO_2$" (second occurrence) should be deleted.

Column 14, line 1, "$NaSO_4$" should be --$Na_2SO_4$--.

Column 14, line 5, "$Ca(PO_4)_2$" should be --$Ca_3(PO_4)_2$--.

Column 14, line 7, "$Ba(PO_4)_2$" should be --$Ba_3(PO_4)_2$--.

Column 14, line 10, "silicates" should be --silicate--.

Column 14, line 15, "$NaCO_3$" should be --$Na_2CO_3$--.

Column 14, line 20, "$Da_3(PO_4)_2$" should be --$Ba_3(PO_4)_2$--.

Column 14, line 24, "$LiSO_4$" should be --$Li_2SO_4$--.

Column 14, line 46, insert a space between "$BaSO_4$," and "$Ba_3(PO_4)_2$".

UNITED STATES PATENT AND TRADEMARK OFFICE
CERTIFICATE OF CORRECTION

PATENT NO. : 4,939,312

DATED : July 3, 1990

INVENTOR(S) : Baerns, et al.

It is certified that error appears in the above-identified patent and that said Letters Patent is hereby corrected as shown below:

Column 14, line 48, "$PBSO_4$" should be --$PbSO_4$--.

Column 14, line 52, "$Ca(PO_4)_2$" should be --$Ca_3(PO_4)_2$--.

Signed and Sealed this

Ninth Day of June, 1992

Attest:

DOUGLAS B. COMER

*Attesting Officer*   *Acting Commissioner of Patents and Trademarks*

UNITED STATES PATENT AND TRADEMARK OFFICE
CERTIFICATE OF CORRECTION

PATENT NO. : 4,939,312

DATED : July 3, 1990

INVENTOR(S) : Baerns, et al.

It is certified that error appears in the above-identified patent and that said Letters Patent is hereby corrected as shown below:

Column 3, line 17, "$Nap_2CO_3$" should be --$Na_2CO_3$--.

Column 3, line 34, "and-mechanic" should be --and mechanic--.

Column 4, line 51, "(b1)" should be --(1)--.

Column 4, line 55, between "impregnation" and "the", insert --:-- (a colon).

Column 5, line 5, "Catalyst K-2" should be centered.

Column 6, line 30, "bidistill" should be --bidistilled--.

Column 6, line 41, "$MgSO_4.7H_2$ O" should be --$MgSO_4.7H_2O$--.

Column 8, line 40, "$Ca(OH)2$" should be --$Ca(OH)_2$--.

Column 8, line 63, after "preparation", insert --)--.

Column 9, line 4, "$Ca(OH)2$" should be --$Ca(OH)_2$--.

Column 9, line 13, delete "distilled".

Column 10, line 15, "al" should be --all--.

Column 10, line 27 (equation), "CH4" should be --$CH_4$--.

Column 11, line 31, "Cn Hm" should be --$C_nH_m$--.

Column 11, line 33, delete the comma between "comprise" and "introducing".

UNITED STATES PATENT AND TRADEMARK OFFICE
CERTIFICATE OF CORRECTION

PATENT NO. : 4,939,312

DATED : July 3, 1990

INVENTOR(S) : Baerns, et al.

It is certified that error appears in the above-identified patent and that said Letters Patent is hereby corrected as shown below:

Column 11, line 37, after "oxygen" insert --between 1 and 20, and contacting methane and oxygen--.

Column 11, lines 42-45, after "Cs", delete "Be, Sr and Ba, and carbonates, sulfates, phosphates and silicates of elements selected from the group consisting of Pb, Sn, Ge, Mg and Ca.

Column 11, line 50, "SIC" should be --SiC--.

Column 11, line 53, "$C_nH_M$" should be --$C_nH_m$--.

Column 11, line 54, "((" should be --(--.

Column 12, line 42, "$KSO_4$" should be --$K_2SO_4$--.

Column 12, line 47, "$SiO_2$" should be --$SrO_2$--.

Column 12, line 48, "$DaCO_3$" should be --$BaCO_3$--.

Column 12, line 48, "use" should be --used--.

Column 13, line 8, "$DaSO_4$" should be --$BaSO_4$--.

Column 13, lines 8-9, "$Ba(PO_4)_2$" should be --$Ba_3(PO_4)_2$--.

Column 13, lines 14-15, between "$Li_2SO_4$" and "$Na_2O_2$", insert --$Na_2O$--.

Column 13, line 20, "$Sr(PO_4)_2$" should be --$Sr_3(PO_4)_2$--.

Column 13, line 39, "containing" should be --contacting--.

Column 13, line 46, "PB" should be --Pb--.

UNITED STATES PATENT AND TRADEMARK OFFICE
CERTIFICATE OF CORRECTION

PATENT NO. : 4,939,312

DATED : July 3, 1990

INVENTOR(S) : Baerns, et al.

It is certified that error appears in the above-identified patent and that said Letters Patent is hereby corrected as shown below:

Column 13, line 47, "where in" should be --wherein--.

Column 13, line 56, "$NaO_2$" (second occurrence) should be deleted.

Column 14, line 1, "$NaSO_4$" should be --$Na_2SO_4$--.

Column 14, line 5, "$Ca(PO_4)_2$" should be --$Ca_3(PO_4)_2$--.

Column 14, line 7, "$Ba(PO_4)_2$" should be --$Ba_3(PO_4)_2$--.

Column 14, line 10, "silicates" should be --silicate--.

Column 14, line 15, "$NaCO_3$" should be --$Na_2CO_3$--.

Column 14, line 20, "$Da_3(PO_4)_2$" should be --$Ba_3(PO_4)_2$--.

Column 14, line 24, "$LiSO_4$" should be --$Li_2SO_4$--.

Column 14, line 46, insert a space between "$BaSO_4$," and "$Ba_3(PO_4)_2$".

UNITED STATES PATENT AND TRADEMARK OFFICE
CERTIFICATE OF CORRECTION

PATENT NO. : 4,939,312

DATED : July 3, 1990

INVENTOR(S) : Baerns, et al.

It is certified that error appears in the above-identified patent and that said Letters Patent is hereby corrected as shown below:

Column 14, line 48, "$PBSO_4$" should be --$PbSO_4$--.

Column 14, line 52, "$Ca(PO_4)_2$" should be --$Ca_3(PO_4)_2$--.

This certicate supersedes Certificate of Correction issued June 9, 1992.

Signed and Sealed this

First Day of September, 1992

Attest:

DOUGLAS B. COMER

*Attesting Officer*    Acting Commissioner of Patents and Trademarks